US005541345A

United States Patent [19]
Hertel et al.

[11] Patent Number: 5,541,345
[45] Date of Patent: Jul. 30, 1996

[54] ANOMERIC FLUORORIBOSYL AMINES

[75] Inventors: Larry W. Hertel; Charles D. Jones; Julian S. Kroin; Thomas E. Mabry, all of Indianapolis, Ind.

[73] Assignee: Eli Lilly and Company, Indianapolis, Ind.

[21] Appl. No.: 453,736

[22] Filed: May 30, 1995

Related U.S. Application Data

[62] Division of Ser. No. 122,876, Sep. 19, 1993, Pat. No. 5,480,992.
[51] Int. Cl.$^6$ .................. C07D 307/12; C07D 307/20; C07D 307/22
[52] U.S. Cl. .................. 549/475; 549/214; 549/480; 549/497; 549/504; 552/1; 552/8
[58] Field of Search .................. 549/475, 480, 549/497, 504, 214; 552/1, 8

[56] References Cited

U.S. PATENT DOCUMENTS

| | | | |
|---|---|---|---|
| 4,526,988 | 6/1985 | Hertel | 549/313 |
| 4,808,614 | 2/1989 | Hertel | 514/45 |
| 4,879,377 | 11/1989 | Brundidge et al. | 536/18.2 |
| 4,965,374 | 10/1990 | Chou, et al. | 549/313 |
| 5,118,820 | 6/1992 | Hertel | 549/313 |

FOREIGN PATENT DOCUMENTS

| | | |
|---|---|---|
| 0184365 | 12/1984 | European Pat. Off. |
| 0345751 | 6/1988 | European Pat. Off. |

OTHER PUBLICATIONS

Anton Stimack et al., *Carbohydrate Research*, 232, pp. 359–365 (1992).

Maria Jose Camarasa et al., *Carbohydrate Research*, 83, pp. 152–156 (1980).

Abderrahime Bouali et al., *J. Carbohydrate Chemistry*, 11 (2), pp. 159–169 (1992).

Alain Guiller et al., *J. Carbohydrate Chemistry*, 5(2), pp. 161–168 (1986).

Kamaliah Kadir et al., *J. Chem. Soc. Perkin I*, pp. 2304–2309.

Cusak, N.J., et al., *J. Chem. Soc. Perkin I*, 1:73–81 (1974).

Cusak, N.J., et al., *Chemical Communications*, 190–191 (1971).

Lofthouse, R., et al., *J. Chem. Soc. Perkin I*, 9:997–1002 (1977).

Li, C., et al., *Tetrahedron Letters*, 34(22):3535–3538 (1993).

Primary Examiner—Ba Kim Trinh
Attorney, Agent, or Firm—Margaret M. Brumm; David E. Boone

[57] ABSTRACT

Anomeric 2,2-difluororibosyl azide and amine intermediates which are useful for the preparation of 2'-deoxynucleosides, and processes thereto, are provided. Processes for preparing 2'-deoxynucleosides also are provided.

11 Claims, No Drawings

ANOMERIC FLUORORIBOSYL AMINES

This application is a division of application Ser. No. 08/122,876, filed Sep. 16, 1993, now U.S. Pat. No. 5,480,992.

FIELD OF THE INVENTION

This invention relates to the fields of pharmaceutical and organic chemistry, and provides novel anomeric 2,2-difluororibosyl azide intermediates and 2,2-difluororibosyl amine intermediates, each of which is useful in the preparation of 2'-deoxy-2',2'-difluoronucleosides. The invention further relates to processes for preparing intermediate and pharmacologically active compounds.

BACKGROUND OF THE INVENTION

Methods for preparing 2'-deoxynucleosides for use as antiviral and antineoplastic agents are generally known in the art of pharmaceutical chemistry. Typically, the art teaches that 2'-deoxynucleosides may be prepared by first preparing a desired carbohydrate, independently preparing a desired base, and condensing the two components to form the desired product (see, e.g., U.S. Pat. No. 5,118,820).

More specifically, U.S. Pat. No. 4,965,374 ('374) discloses the preparation of protected 2,2-difluorolactone intermediates having up to two centers of chirality. One such intermediates having a chiral centers of consists of erythro and threo enantiomers of the formulae

[Structures: erythro and threo]

wherein P is a protecting group. The patent teaches the erythro enantiomer, which is preferred, because it provides a carbohydrate which has the stereochemistry of naturally occurring ribose. A carbohydrate having the stereochemistry of naturally occurring ribose is preferred because it provides final product nucleosides which exhibit superior biological activity.

A second intermediate, taught in the U.S. Pat. No. 4,965,374, possesses a third chiral center which is produced at the anomeric C-1 carbon atom when the carbonyl portion of the lactone is converted to the respective alcohol. The two resulting anomers for the desired erythro configuration are identified as α and β anomers of the formulae

[Structures: alpha and beta]

In this method of preparing 2,2-difluoronucleosides, the hydroxy group at the 1-position is ultimately replaced by a heterocyclic base such as cytosine to provide protected precursors to the biologically active 2'-deoxy-2',2'-difluoronucleosides. This β-anomer precursor is preferred because it provides, after deprotection, 2'-deoxy-2',2'-difluoronucleosides which possess superior biological activity.

In expanding the art of 2'-deoxy-2', 2'-difluoronucleoside preparation, the present invention provides novel intermediates which are useful for the preparation of 2'-deoxynucleosides having pharmacological activity. Also provided are convenient processes for the preparation of such novel intermediates and pharmacologically active compounds.

SUMMARY OF THE INVENTION

The present invention provides compounds of formula I

[Structure: formula I]

or a mixture thereof, wherein
  each $R^2$ is H or each $R^2$ is the same or different hydroxy protecting group;
or a salt thereof, which are useful as intermediates for the preparation of 2'-deoxynucleosides having pharmacological activity.

Also provided are compounds of formula II

[Structure: formula II]

or a mixture thereof,
  wherein each $R^{2'}$ is the same or different hydroxy protecting group. Compounds of formula II also are useful intermediates for the preparation of 2'-deoxynucleosides.

The present invention further provides a process for preparing compounds of formula I which comprises
  a) reacting a compound of formula III

[Structure: formula III]

or a mixture thereof, wherein
  $R^1$ is a leaving group; and
  $R^{2'}$ is as defined above, with an azide nucleophile;
  b) reducing the reaction product from step a); and
  c) optionally salifying the reaction product from step b).

The present invention also provides a process for preparing a compound of formula V

[Structure: formula V]

wherein
  $R^2$ is as defined above;

$R^3$ is H, $C_1$–$C_4$ alkyl, bromo, chloro, fluoro or iodo; and
$R^4$ is $NH_2$ or OH (or a tautomer thereof);
or a salt thereof, which comprises the above-described process for preparing a compound of formula I and further comprising d) condensing a compound of formula I with an acyclic compound of formula VI

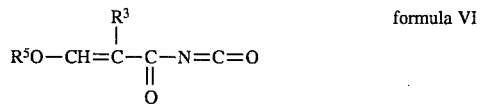

formula VI wherein $R^3$ is as defined above and $R^5$ is $C_1$–$C_4$ alkyl;

e) cyclizing the reaction product from step d);

f) optionally deprotecting the reaction product froin step e);

g) optionally converting the 4-position hydroxy functionality of the reaction product from step f) with an amine group; and h) optionally salifying the reaction product from step g).

DETAILED DESCRIPTION OF THE INVENTION

The term "$C_1$–$C_4$ alkyl" refers to straight or branched aliphatic chains of 1–4 carbon atoms such as, for example, methyl, ethyl, propyl, isopropyl, n-butyl, isobutyl, sec-butyl, and tert-butyl.

The term "or a mixture thereof" refers to more than one stereochemical configuration of a particular compound described herein which possesses one or more chiral centers.

The present invention relates to novel intermediates which are useful for the preparation of 2'-deoxynucleosides having pharmacological activity.

The starting materials, represented by compounds of formula III,

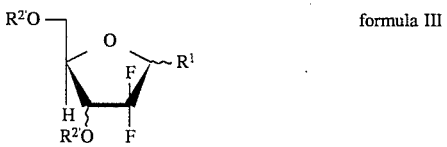

formula III or a mixture thereof, wherein $R^1$ is a leaving group;

each $R^{2'}$ is the same or different hydroxy protecting group; and

The term "or a tautomer thereof" indicates that the $R^4$ substituent of formula V compounds (OH or $NH_2$), is in equilibrium with its recognized tautomeric form. For example, it is understood that a hydroxy $R^4$ substituent of a particular formula V compound is in a tautomeric relationship with the keto form of that compound.

Formula III compounds can be prepared by the method taught by Chou, et al. in U.S. Pat. No. 4,965,374. This patent, relative to the preparation of compounds of formula III, is herein incorporated by reference.

Appropriate $R^1$ leaving groups for formula III compounds include the sulfonates such as methanesulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as iodo, bromo, chloro and the like, and other related leaving groups. A preferred leaving group is trillate, while methanesulfonate and bromo are especially preferred.

The $R^{2'}$ substituents of compounds of formulae II, III, and IV, and the $R^2$ substituents of compounds of formulae I and V, when $R^2$ is not H, each represent the same or different hydroxy protecting group. Such a protecting group generally is not found in the final therapeutic compound but is intentionally introduced during a portion of the synthetic process to protect a group which otherwise might react in the course of chemical manipulations, and is then removed at a later stage of the synthesis. Numerous reactions for the formation and removal of such protecting groups are described in a number of standard works including, for example, *Protective Groups in Organic Chemistry* 7, Plenum Press (London and New York, 1973); Green, Th. W., *Protective Groups in Organic Synthesis* 7, Wiley (New York, 1981); and *The Peptides* 7, Vol. I, Schrooder and Lubke, Academic Press (London and New York, 1965).

Although Chou, et al., supra, teach that benzoyl is the preferred hydroxy protecting group, other protecting groups may be used. Such alternative groups include ester forming groups such as formyl, acetyl, substituted acetyl, propionyl, butanoyl, pivaloylamido, 2-chloroacetyl, substituted benzoyl, phenoxyacetyl, methoxyacetyl, and the like, carbonate derivatives such as phenoxycarbonyl, ethoxycarbonyl, t-butoxycarbonyl, vinyloxycarbonyl, 2,2,2-trichloroethoxycarbonyl, benzyloxycarbonyl, and the like, alkyl ether forming groups such as benzyl, diphenylmethyl, triphenylmethyl, t-butyl, methoxymethyl, tetrahydropyranyl, allyl, tetrahydrothienyl, 2-methoxyethoxymethyl, and the like, and silyl ether forming groups such as trialkylsilyl, trimethylsilyl, isopropyldialkylsilyl, alkyldiisopropylsilyl, triisopropylsilyl, t-butyldialkylsilyl, and the like, and carbamates such as N-phenylcarbamate and N-imidazoylcarbamate, and the like. Of these, benzoyl and t-butyldimethylsilyl are preferred.

As depicted above, the wavy lines shown at the 1- and 3-positions of formulae I, II, III and VII indicate that the stereochemistry of these compounds may vary. All configurations of each compound represented by these formulae are believed to be useful, and the stereochemistry of a compound is not to be construed as a limitation to the present invention. However, the preferred starting material generally possesses the stereochemistry of naturally-occurring ribose shown in formula IV

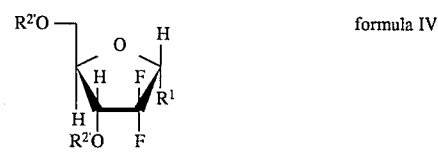

formula IV wherein $R^1$ and $R^{2'}$ as defined above.

Novel intermediates of formula II are prepared by reacting a compound of formula III with an equimolar to excess amount of an azide nucleophile. Typical azide nucleophiles include the alkali metal azides such as lithium azide, sodium azide, potassium azide, and the like, quarternary amine azides such as tetrabutylammonium azide, and the like, and tetramethylguanidinium azide (TGMA). Lithium azide and TGMA are preferred. This reaction is shown below in Reaction I.

Reaction I

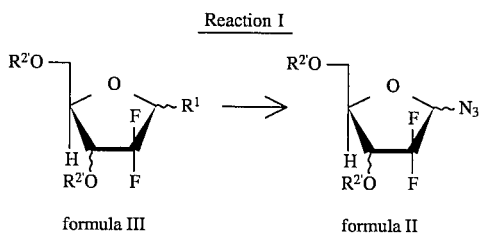

formula III → formula II

Reaction II

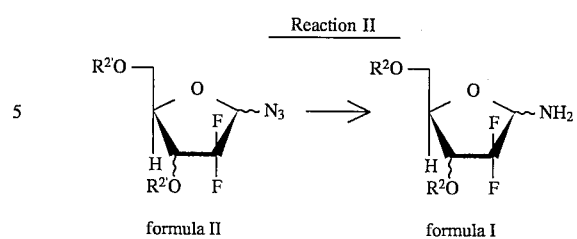

formula II → formula I wherein $R^1$ and $R^{2'}$ are as defined above.

This reaction is carried out in the presence of one or more suitable solvents at a temperature from about 25° C. to about 100° C. under an inert atmosphere. Suitable solvents include the aprotic solvents while N,N-dimethylformamide (DMF) is preferred when lithium azide is used as the azide nucleophile, and chloroform is preferred with TMGA.

TIle amount of time needed for these reactions to run to completion will be recognized by one of ordinary skill in the art. Although chromatographic assay methods such as TLC or HPLC will assist in determining the completion of these reactions, they generally are completed from about a few hours to about 10 hours.

In Reaction I, the stereochemistry of formula II compounds primarily is dictated by the stereochemistry of the selected formula III starting material. When an α-anomer of a formula III compound is selected as the starting material and reacted with an azide nucleophile as described above, the resulting formula II compound substantially will have the β-configuration. Likewise, when β-anomer of a formula III compound is selected as a starting material, the resulting pro. duct substantially will have the α-configuration. Thus α-anomers, β-anomers, and α-, β-mixtures of formula iI compounds each are important aspects of the present invention.

The stereochemistry of the 3-position protected hydroxy functionality also is dictated by the stereochemistry of the starting material. Thus, if a starting material possesses an erythro configuration at the 3-position protected hydroxy substituent and an α-configured leaving group at the 1-position, the resulting azide of formula II substantially will possess the same stereochemistry at the C-3 center, but the 1α-positioned leaving group is replaced by a 1β-position azido group. The present invention, therefore, includes diasteromeric compounds of formula II which possess the erythro-configuration, the threo configuration, and combinations thereof at the 3-position, and the various above-described 1-position configurations and mixtures thereof.

Formula II compounds are useful intermediates in the preparation of 2'-deoxynucleosides having, inter alia, pharmacological activity.

Compounds of formula I are prepared by reducing the azido moiety of formula II compounds to give the corresponding amine. This reaction, shown below in Reaction II, is accomplished by using one of the numerous reduction reactions which are well known to one skilled in the organic chemical arts. However, catalytic hydrogenation is preferred.

or a mixture thereof, wherein $R^2$ and $R^{2'}$ are as defined above, or a salt of a compound of formula I.

In Reaction II, a formula II compound (a product of Reaction I) is catalytically hydrogenated in the presence of a suitable solvent or mixture of solvents to form a compound of formula I.

Suitable hydrogenation catalysts include noble metals and oxides such as palladium, platinum and rhodium oxide on a support such as carbon or calcium carbonate. However, palladium-on-carbon and palladium-on-calcium carbonate are preferred.

Solvents for this reaction are those solvents or mixture of solvents which remain inert throughout the reaction. Typically, alcohols and, especially, ethyl acetate, are suitable solvents.

The temperature employed in this step should be sufficient to effect completion of the hydrogenation reaction. Typically, ambient temperature is sufficient and preferred.

One skilled in the art will recognize that this reaction may be conducted under pressure of from about 20 psi to about 60 psi. If the reaction is not run at ambient pressure, about 40 psi is preferred.

A product of Reaction II substantially will maintain the 3-position stereochemistry of its starting material. Thus, if a compound of formula II possesses a 3-position erythro configuration, the formula I product of Reaction II also will substantially possess that configuration. Because the 3-position stereochemistry of a Reaction I starting material also is substantially maintained in the reaction product thereof, the preferred erythro configuration of 3-position substituents may be substantially maintained throughout the processes depicted in Reaction I and Reaction II.

In the second step of the present process (Reaction II), the product substantially will possess a 1:1 ratio of α- and β-configured anomers regardless of the stereochemistry of the formula II reactant. However, one skilled in the art should be able to separate the preferred α-anomer through the use of standard techniques. Thus, the novel reaction products of Reaction II, compounds of formula I, may have various stereochemical configurations, but a formula I compound having a 1-position β-configuration and a 3-position erythro configuration is preferred.

As mentioned above, the present invention also includes a salt form of formula I compounds. Thus, formula I compounds may be reacted with any number of inorganic and organic acids to form an acid addition salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such salts are sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and those formed with organic acids such as maleic acid and methanesulfonic acid. Of the preferred acids, hydrochloric acid is especially preferred.

The $R^2$ hydroxy protecting groups of formula I compounds may be removed (deprotection, including hydrogenation) prior to or following the cyclization process described below. When deprotection occurs prior to cyclization, the deprotection step may be carried out in the same vessel as are above-described steps a) and b). Deprotection is accomplished using methods well known in the art and provides compounds of formula Ib:

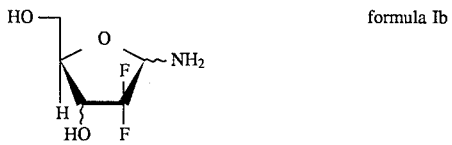

or a mixture thereof, for a salt thereof.

Preferably, formula Ib compounds are prepared as salts by treating a compound of formula Ia

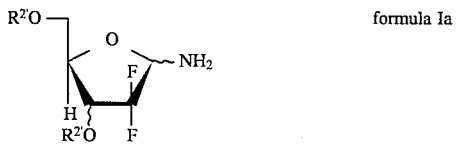

or a mixture thereof, wherein $R^{2'}$ is as defined above, in a suitable solvent or mixture of solvents with an anhydrous acid, such as anhydrous hydrogen bromide and the like, to saturation.

Suitable solvents or mixtures of solvents are those which remain inert throughout the preparation of formula Ib compounds. Dichloromethane is preferred.

Typically, the preparation of formula Ib compounds is accomplished under ambient temperature. However, the optimum temperature for this reaction is easily found according to routine skill in the art.

One of ordinary skill in the art will also recognize the amount of time needed to prepare formula Ib compounds from formula Ia compounds. Generally, this reaction is completed in from about a few hours to about 10 hours.

In the preparation of formula Ia and Ib compounds, the processes may be carried out as independent steps wherein the reaction product from each step is isolated and purified, or, preferably, carried out in situ as a process wherein each step of the process is sequentially carried out in the same vessel.

In another aspect of the present invention, 2'-deoxynucleosides are prepared by the process for preparing compounds of formula I, and the following additional steps.

A 2'-deoxynucleoside can be prepared by condensing an anomeric amine of formula Ia or Ib, herein collectively designated as formula I compounds, with an acryloyl or acrylamine derivative and cyclizing the reaction product from the condensation step to give a natural or unnatural base condensed with a formula I compound. This aspect of the present process is well known in the art and is described by, for example, Cusack, et al., *J. Chem. Soc. Perkin I,* 1:73–81 (1974); Cusack, et al., *Chemical Communications,* 190–191 (1971); and Lofthouse, et al., *J. Chem. Soc. Perkin I,* 9:997–1002 (1977).

Preferably, the anomeric amine of formula I is in a protected form (when each $R^2$ is a hydroxy protecting group) prior to the condensation step. Following cyclization, the reaction product optionally is deprotected via standard procedures known in the art, optionally aminated at the 4-position of the cyclized base, and the product of the amination step optionally is salified via known procedures.

Thus, another aspect of the present invention is a process for preparing a compound of formula V

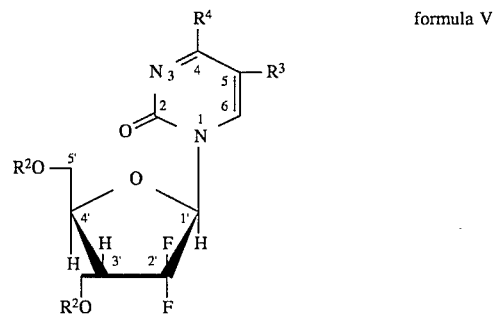

wherein $R^2$ is defined above;

$R^3$ is H, $C_1$–$C_4$ alkyl, bromo, chloro, fluoro or iodo; and $R^4$ is $NH_2$ or OH (or a tautomer thereof); or a salt thereof, which comprises the above-described process for preparing a compound of formula I and further comprising d) condensing a compound of formula I with an acyclic compound of formula VI

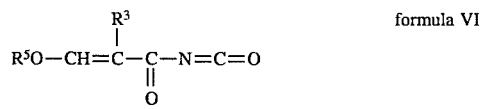

wherein $R^3$ is as defined above and $R^5$ is $C_1$–$C_4$ alkyl;

e) cyclizing the reaction product from step d);

f) optionally deprotecting the reaction product from step e);

g) optionally converting the 4-position hydroxy functionality of the reaction product from step f) with an amine group; and h) optionally salifying the reaction product from step g).

This process can be used to prepare the preferred compounds of formula V where $R^3$ is H and $R^4$ is $NH_2$.

In order that the invention described herein may be more fully understood, the following examples are set forth. It should be understood, however, that these examples are only for illustrative purposes and are not to be construed as limiting the scope of this invention in any manner.

EXAMPLE 1

1-α-Azido-2-deoxy-2,2-difluoro-D-ribofuranosyl-3,5-di-O-benzoate

To a solution of 0.2 g of 2-deoxy-2,2-difluoro-D-ribofuranosyl- 3,5-di-O-benzoyl-1-O-β-methanesulfonate in 5.0 mL of DMF was added 0.214 g of $LiN_3$ and the resulting mixture heated in a 70° C. oil bath under $N_2$ atmosphere for 4 hours. The starting material was completely consumed as judged by TLC (SiO$_2$, EtOAc/toluene 2:8). After allowing the reaction to cool to 23° C., it was poured into brine. The crude product was extracted with EtOAc, dried over MgSO$_4$ and concentrated to an oil which was chromatographed (LP-1, toluene) to give 0.129 g (73%) of a colorless oil which crystallized on standing; mp 72°–3° C. 1H NMR (300 MHz, DMF-d$_7$) δ4.66 ppm (dd, 2H, H5), 4.93 (q, 1H, H4), 5.59 (dd, J=15.0, 6.0 Hz, 1H, H3), 6.17 (d, J=11.0 Hz, 1H, H1), 7.4–7.5 (m, 4H, Ar-meta), 7.53–7.64 (m 2H, Ar-para), 7.85–8.0 (m 4H, Ar-ortho); FDMS 405+ (m+2), 361+ (m-N$_3$); IR (CHCl$_3$) 2123, 1727, 1317 Cm$^{-1}$.

EXAMPLE 2

1-α-Azido-2-deoxy-2,2-difluoro-D-ribofuranosyl-3,5-di-O-benzoate

To a solution of 0.0116 g of 2-deoxy-2,2-difluoro-D-ribofuranosyl- 3,5-di-O-benzoyl-1-β-(p-bromobenzene) sulfonate in 2.0 mL of DMF-d7 was added 0.097 g of LiN$_3$ and the resulting mixture was heated in a 70° C. oil bath under N$_2$ atmosphere for 4 hours. The starting material was completely consumed as judged by TLC (SiO$_2$, EtOAc/toluene 2:8). The $^1$H NMR spectrum indicated the major product, which was formed in >90% conversion, to be identical to the compound isolated in Example 1.

EXAMPLE 3

1-β-Azido-2-deoxy-2,2-difluoro-D-ribofuranosyl-3,5-di-O-benzoate

To a solution of 0.2 9 of 2-deoxy-2,2-difluoro-D-ribofuranosyl- 3,5-di-O-benzoyl-1-O-α-methanesulfonate in 5.0 ml of DMF was added 0.214 g of LiN$_3$ and the resulting mixture was heated in a 70° C. oil bath under N$_2$ atmosphere for 4 hours. The starting material was completely consumed as judged by TLC (SiO$_2$, EtOAc/toluene 2:8). After allowing the reaction to cool to 23° C., it was poured into brine. The crude product was extracted with EtOAc, dried over MgSO$_4$ and concentrated to an oil which was chromatographed (LP-1, toluene) to give 0.133 g (76%) of a colorless oil which crystallized on standing, mp 63°–4° C. $^1$H NMR (300 MHz, DMFd-$_7$) δ4.69 ppm (m, 2H, H5), 4.78 (m, 1H, H4), 5.79 (m, 1H, H3 ), 5.86 ( dd, J=5.4 Hz, 1H, H1 ), 7.42–7.56 (m, 4H, Armeta), 7.59–7.7 (m 2H, Ar-para), 8.01 (m 4H, Ar-ortho); FDMS 405+ (m+2), 361+ (m-N$_3$); IR (CHCl$_3$) 2123, 1728, 1452 cm$^{-1}$.

EXAMPLE 4

1-β-Azido-2-deoxy-2,2-difluoro-D-ribofuranosyl-3,5-di-O-benzoate

To a solution of 0.390 g of 2-deoxy-2,2-difluoro-D-ribofuranosyl- 3,5-di-O-benzoyl-1-60 -bromide in 5.0 mL of DMF was added 0.432 g of LiN$_3$ and the resulting mixture was heated to 70° C. under N$_2$ atmosphere for 6 hours. The starting material was completely consumed as judged by TLC (SiO$_2$, EtOAc/toluene 2:8). After allowing the reaction mixture to cool to 23° C., it was poured into brine. The crude product was extracted with EtOAc, dried over MgSO$_4$ and concentrated to an oil which was chromatographed (SiO$_2$ toluene) to give 0.210 g (60%) of a colorless oil which crystallized on standing. The $^1$H NMR spectrum was identical to the compound isolated in Example 3.

EXAMPLE 5

3,5-bis(t-butyldimethylsilyloxy)-1-α/β-azido-2-deoxy-2,2-difluororibose

To 1.3 g of 3,5-bis (t-butyldimethylsilyoxy) -1-methanesulfonyloxy- 2-deoxy-2,2-difluororibose in 10 mL of DMF over 3A molecular sieves was added 0.40 g of lithium azide. After stirring overnight at ambient temperature, the solution was poured onto ice. The organic layer was washed with water, dried over Na$_2$SO$_4$, and concentrated in vacuo at 40° C. to obtain 1.1 g of the title compound. $^1$H NMR (300MHz, CDCl$_3$); for the β anomer δ0.035–0.129 (m, 12H) , 0.86–0.91 (m, 18H), 3.68–3. 875 (series of m, 3H, H4 and H5), 5.04 (dd, 1H, H1); for the α anomer δ0.035–0.129 (m, 12H) , 0.86–0.91 (m, 18H) , 3.68–3. 875 (series of m, 3H, H4 and H5), 5.13 (dd, 1H, H1); MS 366 (Parent; loss of t-butyl); IR (CHCl$_3$) 2123 cm$^{-1}$.

EXAMPLE 6

1-α/β-Amino-2-deoxy-2,2-difluoro-D-ribofuranosyl-3,5-di-O-benzoate

A 1:1 α/β- mixture of 1-azido-2-deoxy-2,2-difluoro-D-ribofuranosyl- 3,5-di-O-benzoate (1.0 g) in 20.0 mL of EtOAc was hydrogenated over 0.05 g of 5% Pd/CaCO$_3$ under H$_2$ atmosphere at 23° C. and ambient pressure. The starting material was completely consumed after 1 hour as judged by TLC (SiO$_2$, EtOAc/toluene 2:8). The mixture was filtered through Celite® and the filtrate concentrated to give 0.91 g (97%) of a colorless oil; $^1$H NMR (CDCl$_3$) δ2.22 (d, 2H, NH$_2$), 4.30 (m, 0.66H, H5), 4.71–4.51 (m, 2.33H, H4' and H5'), 4.86 (m, 0.66H, H3), 5.12 (m, 0.33H, H3), 5.48 (m, 0.66H, Hi), 5.7 (m, 0.33H, H1), 7.4–7.5 (m, 4H, Ar), 7.53–7.64 (m, 2H, Ar), 7.85–8.0 (m, 4H, Ar); FDMS 378+ (m+2); IR (CHCl$_3$) 1726, 1602, 1452 cm$^{-1}$; C$_{19}$H$_{17}$F$_2$NO$_5$ requires C, 60.80 H, 4.57 N, 3.73; found: C, 60.80 H, 4.38 N, 3.42.

EXAMPLE 7

3,5-bis(t-butyldimethylsilyloxy)-1-α/β-amino-2-deoxy-2,2,difluororibose 0.5 g of 3,5-bis(t-butyldimethylsilyloxy)-1-α/β-azido-2-deoxy-2,2-difluororibose was hydrogenated for 3 hours over 0.5 g of 5% Pd/C in 3A ethanol under H$_2$ atmosphere at ambient temperature and 40 psi. The mixture was filtered, rinsed with 3A ethanol, and the liltrate was concentrated in vacuo to give 0.45 g of a colorless oil. 1H NMR (CDCl$_3$90 MHz) for the β anomer ∂0.05–0.1 (m, 12H) 0.88–0.89 (m, 18H), 3.6–5.7 (Series of m, 4H, H3, H4, H5) 4.83(t, J=9 Hz, 1H, H1); for the α anomer ∂0.05–0.1 (m, 12H) 0.88–0.89 (m, 18H), 3.6–5.7 (Series of m, 4H, H3, H4,H5) 4.97(t, J=7 Hz, 1H, H1); mass spectroscopy m=340 (parent; loss of t-butyl); IR (loss of azide stretch).

EXAMPLE 8

1-α/β-Amino-2-deoxy-2,2-difluororibose hydrobromide

To 0.19 g of 3,5-bis(t-butyldimethylsilyloxy)-1-α/β-amino- 2-deoxy-2,2-difluororibose in 5.0 mL of dichloromethane was added anhydrous hydrogen bromide to saturation, and the solution was stirred overnight at ambient temperature. The solvent was removed in vacuo at 40° C. to give 0.12 g of a yellow foam. $^1$H NMR (CD$_3$OD 300 MHz) NMR consistant with structure; MS 169.

We claim:

1. A compound of formula I

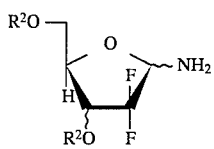

formula I or a mixture thereof,
wherein
 each $R^2$ is H or each $R^2$ is the same or different hydroxy protecting group;
or a salt thereof.

2. A compound of claim 1 having the formula

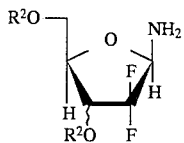

or a mixture thereof, or a salt thereof.

3. A compound of claim 2 having the formula

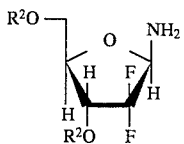

or a salt thereof.

4. A compound of claim 3 wherein each $R^2$ is benzoyl.

5. A compound of claim 3 wherein each $R^2$ is t-butyldimethylsilyl.

6. A hydrobromide salt of a compound of claim 3.

7. A compound of formula II

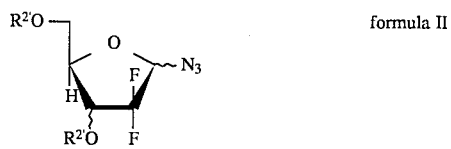

or a mixture thereof,
 wherein each $R^{2'}$ is the same or different hydroxy protecting group.

8. A compound of claim 7 having the formula

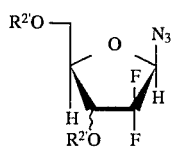

or a mixture thereof.

9. A compound of claim 8 having the formula

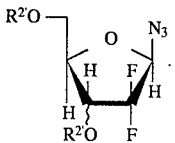

10. A compound of claim 9 wherein each $R^{2'}$ is a benzoyl.

11. A compound of claim 9 wherein each $R^{2'}$ is t-butyldimethylsilyl.

* * * * *